United States Patent [19]

Houghton et al.

[11] Patent Number: 5,378,387
[45] Date of Patent: Jan. 3, 1995

[54] NON-AQUEOUS LIQUID CLEANING PRODUCTS COMPRISING POLYALKOXYLATED DERIVATIVES OF CASTOR OIL RICINOLEIC ACID AND ANALOGOUS FATTY ALCOHOLS

[75] Inventors: Mark P. Houghton, Rotterdam; Charles C. Verburg, Vlaardingen, both of Netherlands

[73] Assignee: Lever Brothers Company, Division of Conopco, Inc., New York, N.Y.

[21] Appl. No.: 71,436

[22] Filed: Jun. 1, 1993

[30] Foreign Application Priority Data

Jun. 2, 1992 [EP] European Pat. Off. ............ 92201565

[51] Int. Cl.$^6$ ...................... C11D 1/72; C11D 1/825; C11D 17/00
[52] U.S. Cl. .................. 252/174.21; 252/94; 252/174; 252/174.22; 252/DIG. 1; 252/DIG. 14
[58] Field of Search ...................... 252/174.21, 174.22, 252/DIG. 1, DIG. 14

[56] References Cited

U.S. PATENT DOCUMENTS

| | | | |
|---|---|---|---|
| 3,312,542 | 4/1967 | Kitzke et al. | 71/2.7 |
| 4,313,847 | 2/1982 | Chasin et al. | 252/356 |
| 4,746,455 | 5/1988 | Matsuda et al. | 252/174.23 |
| 4,774,016 | 9/1988 | Gazzani | 252/170 |
| 5,025,069 | 6/1991 | Deguchi et al. | 252/174.17 |
| 5,154,850 | 10/1992 | Deguchi et al. | 252/174.17 |
| 5,225,112 | 7/1993 | Miyazawa et al. | 252/545 |

FOREIGN PATENT DOCUMENTS

| | | |
|---|---|---|
| 004353 | 10/1979 | European Pat. Off. |
| 280550 | 8/1988 | European Pat. Off. |
| 373483 | 6/1990 | European Pat. Off. |
| 120048 | 5/1976 | Germany . |
| 4009534 | 9/1991 | Germany . |
| 63-207900 | 8/1988 | Japan . |
| 3151620 | 6/1991 | Japan . |
| 253437 | 3/1987 | Switzerland . |
| 1531843 | 11/1978 | United Kingdom . |

OTHER PUBLICATIONS

Chemical Abstract Accession #107:161392, for JP 62-108806, May 20, 1987.
CA98(10):77805x, "Determination of non-ionic detergents in effluents by atomic absorption spectroscopy", Grasso et al., Cuois, Pelli, Mater. Concianti, 58(37, 286–90 (Ital) 1982.
European Search Report & Annex, EP 92201565, Feb. 22, 1993.
Chemical Abstracts, vol. 86, No. 12,-21, Mar. 1977, Abstract No. 74903, p. 126.

Primary Examiner—Paul Lieberman
Assistant Examiner—A. Hertzog
Attorney, Agent, or Firm—Ronald A. Koatz

[57] ABSTRACT

Substantially non-aqueous liquid cleaning compositions comprising a non-aqueous liquid phase that comprises a polyalkoxylated castor oil derivative and/or polyalkoxylated derivatives of ricinoleic acid (set forth as formula (III)) and/or polyalkoxylated derivatives of analogous fatty alcohols (set forth as formula (IV)).

5 Claims, No Drawings

NON-AQUEOUS LIQUID CLEANING PRODUCTS COMPRISING POLYALKOXYLATED DERIVATIVES OF CASTOR OIL RICINOLEIC ACID AND ANALOGOUS FATTY ALCOHOLS

The present invention relates to substantially non-aqueous liquid cleaning products, especially detergent compositions containing particulate solid materials. Non-aqueous liquids are those containing little or no water.

In liquid detergents in general, especially those for the washing of fabrics, it is often desired to disperse or suspend particulate solids which have beneficial auxiliary effects in the wash, for example detergency builders to counteract water hardness, as well as bleaches and enzymes.

In substantially non-aqueous formulations, the solids are dispersed in a non-aqueous liquid phase which usually comprises a liquid nonionic surfactant, optionally also with some non-surfactant liquid. The liquid nonionic surfactant commonly comprises at least one ethoxylated nonionic. In order for the composition to have desirable properties, it is usually preferred to utilise a mixture of liquid nonionics which includes a nonionic having relatively few ethylene-oxy groups per molecule, for example an average of three. However, recently, the low-ethoxy nonionics have been suspected of having an undesirably high aquatic toxicity.

It is also common for such compositions to include a deflocculant such as an anionic surfactant which is added in the free acid form. However, the anionic surfactant tends to worsen the detergency effect of the ethoxylated nonionic.

We have now found that these drawbacks can be overcome, at least in part, if the liquid phase comprises a polyalkoxylated castor oil derivative.

It has further been found that detergent compositions comprising polyalkoxylated castor oil derivative surprisingly show low foaming characteristics.

Thus, in a first aspect the present invention provides a substantially non-aqueous liquid cleaning composition comprising a non-aqueous liquid phase, which liquid phase comprises a polyalkoxylated castor oil derivative.

Preferably, the polyalkoxylated castor oil derivative has the general formula (I)

$$\begin{array}{l} CH_2-R^1 \\ CH-R^2 \\ CH_2-R^3 \end{array} \quad (I)$$

where $R^1$–$R^3$ are independently selected from groups of formula:

$$CH_3-(CH_2)_5-CH-CH_2-CH=CH-(CH_2)_7-CO_2-$$
$$\phantom{CH_3-(CH_2)_5-CH}\backslash$$
$$\phantom{CH_3-(CH_2)_5-CH-CH}OR^4_nH$$

wherein n is from 2 to 16 and each $R^4$ is independently selected from $C_{2-4}$ alkyleneoxy groups.

The parent fatty acid, i.e. of formula (II)

$$CH_3-(CH_2)_5-CH-CH_2-CH=CH-(CH_2)_7-CO_2H \quad (II)$$
$$\phantom{CH_3-(CH_2)_5-CH}\backslash$$
$$\phantom{CH_3-(CH_2)_5-CH-CH}OH$$

is known as ricinoleic acid which is a natural fatty acid. Polyalkoxylated derivatives (of formula (III) as hereinafter defined) of ricinoleic acid and polyalkoxylated derivatives (of formulae (IV) as hereinafter defined) of certain analogous fatty alcohols can also be used in place of, or as well as, the compounds of formula (I). Thus, a second aspect of the present invention provides a substantially non-aqueous liquid cleaning product composition comprising a non-aqueous liquid phase, which liquid phase comprises a compound of formula (III)

$$CH_3-(CH_2)_5-CH-CH_2-CH=CH-(CH_2)_7-CO_2H \quad (III)$$
$$\phantom{CH_3-(CH_2)_5-CH}|$$
$$\phantom{CH_3-(CH_2)_5-CH}OR_n^4H$$

or a salt thereof, wherein $R^4$ and n are as defined in respect of formula (I) or a compound of formula (IV)

$$R^6-(CH_2)_2-R^7 \quad (IV)$$

wherein $R^6$ is a group of formula $$(CH_3)_2C=CH-$$

or a group of formula $$CH_2=C-CH_2-$$
$$\phantom{CH_2=}|$$
$$\phantom{CH_2=}CH_3$$

and $R^7$ is a group of formula $$\phantom{-}CH_3$$
$$\phantom{-}|$$
$$-C-CH=CH_2$$
$$\phantom{-}|$$
$$\phantom{-}CH_3$$

a group of formula $$-CH-(CH_2)_2-OR_n^4$$
$$|$$
$$CH_3$$

or a group of formula $$-C=CH-CH_2-OR_n^4$$
$$|$$
$$CH_3$$

wherein $R^4$ and n are as defined in respect of formula (I).

Among the salts of the acids of formula (III), the alkali metal (e.g. sodium or potassium) or alkaline earth metal (e.g. calcium or magnesium) are preferred. Salts of organic cations, e.g. quaternary ammonium, are also possible.

Any reference hereinafter to a compound of formula (III) is reference to either the acid or the salt form, unless explicitly stated to the contrary.

It will be appreciated that when two or more compounds of formulae (I), (III) and (IV) are present in a composition according to the present invention, the values at $R^4$ and n will not necessarily be the same in each. Moreover, as a result of manufacture, any material according to the formulae (I), (III) and (IV) may contain a spectrum of compounds within the respective general formula and optionally also some impurities.

In formula (I), preferably $R^1$–$R^3$ are the same. In any of formula (I), (III) and (IV), preferably $R^4$ is ethyleneoxy. Most preferably, n is from 8 to 12.

We may also claim in accordance with the present invention, any compound of formula (I), (III) and (IV) as hereinbefore defined. However, compounds of formulae (I), (III) and (IV) in general are either commercially available materials or else they may be prepared by techniques well known to those skilled in the art of synthetic organic chemistry, especially methods used in the manufacture of conventional polyalkoxylated nonionic surfactants from their corresponding fatty alcohols. Some of the parent fatty alcohols corresponding to the polyalkoxylated derivatives of formula (IV) and which may be used as starting materials in the preparation of some, are as follows:

Limalool is the alcohol of formula (V)

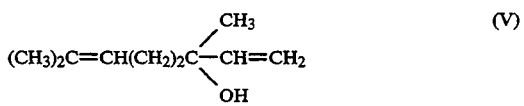

citronellol is the alcohol of formula (VI)

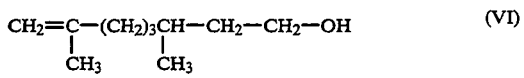

rhodinol is the alcohol of formula (VII)

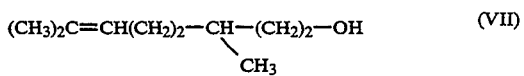

and geraniol is the alcohol of formula (VIII)

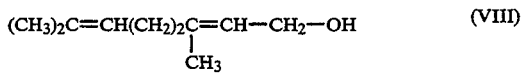

Compositions of the present invention also, in many instances, demonstrate less clear layer formation due to sedimentation of the solids, relative to conventional non-aqueous dispersions.

Thus, in a further aspect the present invention provides a substantially non-aqueous liquid cleaning composition comprising a particulate solid phase dispersed in a non-aqueous liquid phase, which liquid phase comprises a polyalkoxylated castor oil derivative or a compound of formula (III) or a compound of formula (IV).

In the following, the term "polyalkoxylated derivative of the invention" refers to any material of formula (I), (II) or (III) as hereinbefore defined, whether or not novel.

Generally it is preferred for the liquid phase to comprise both a polyalkoxylated derivative of the invention and also a nonionic surfactant which is an polyalkoxylated adduct of a fatty alcohol. Of these, especially preferred are those ethoxylated nonionic surfactants with a hydrophobichydrophilic balance (HLB) of at least 10, preferably at least 12.5. Suitable examples include the liquid condensation products of fatty alcohols with from 12 to 15 carbon atoms condensed with at least 5, preferably from 6 to 11 moles of ethylene oxide. Examples of these are the condensation products of C11-13 alcohols with 6 to 11 moles of ethylene oxide.

For ethoxylated nonionic surfactants, a convenient way of calculating the HLB is by the formula $$HLB = \frac{20 \times MW(EO)}{MW(TOT)}$$

where MW(EO) is the molecular weight of the ethylene oxide part of the surfactant molecule and MW(TOT) is the molecular weight of the total surfactant molecule.

It is possible to include some nonionic surfactants with lower HLB values, i.e. with fewer ethylene oxide groups per molecule, although such compositions are generally less preferred.

Using a mixture of both a polyalkoxylated derivative of the invention and a polyalkoxylated fatty alcohol adduct has been found not only to improve detergency in the wash but also to reduce the viscosity of the overall composition. This viscosity reducing effect is much more marked in compositions according to the present invention as compared with corresponding compositions without any dispersed solids.

In such mixtures the amount of the polyalkoxylated castor oil derivative may be for example 10%, 20%, 30%, 40%, 50%, 60%, 70%, 80% or 90% by weight of the liquid phase.

Similarly, the amount of the polyalkoxylated fatty alcohol adduct may also be, for example, 10%, 20%, 30%, 40%, 50%, 60%, 70%, 80% or 90% by weight of the liquid phase.

PRODUCT FORM

All compositions according to the present invention are liquid cleaning products. In the context of this specification, all references to liquid cleaning products refer to those product materials which are liquid at 25° C. at atmospheric pressure. They may be formulated in a very wide range of specific forms, according to the intended use. They may be formulated as cleaners for hard surfaces (with or without abrasive) or as agents for warewashing (cleaning of dishes, cutlery etc) either by hand or mechanical means, as well as in the form of specialised cleaning products, such as for surgical apparatus or artificial dentures. Preferably compositions of the invention are formulated as agents for washing and-/or conditioning of fabrics.

Thus, the compositions will contain at least one agent which promotes the cleaning and/or conditioning of the article(s) in question, selected according to the intended application. Usually, this agent will be selected from surfactants, enzymes, bleaches, builders, buffers, microbiocides, (for fabrics) fabric softening agents and (in the case of hard surface cleaning) abrasives. Of course in many cases, more than one of these agents will be present, as well as other ingredients commonly used in the relevant product form.

If compositions of the invention are fabric cleaning products they preferably contain a liquid phase containing nonionic surfactants and a solid phase dispersed in the liquid phase, said solid phase comprising one or more of the following ingredients bleaches, bleach activators, builders and solid surfactants. If compositions of the invention are intended for other uses, for example for mechanical warewashing, sometimes the liquid phase will comprise a solvent material other than nonionic surfactant such as for example glyceroltriacetate, paraffin, a low molecular weight polyethylene glycol or an ethoxylated polyethylene glycol. The solid phase of the product will then generally comprise one or more of builders, abrasive materials and solid surfactant materials.

SURFACTANT

Where surfactants are solids, they will usually be dissolved or dispersed in the liquid phase. Where they are liquids, they will usually constitute all or part of the liquid phase. However, in some cases the surfactants may undergo a phase change in the composition.

In general, surfactants for use in the compositions of the invention may be chosen from any of the classes, sub-classes and specific materials described in "Surface Active Agents" Vol. I, by Schwartz & Perry, Interscience 1949 and "Surface Active Agents" Vol. II by Schwartz, Perry & Berch (Interscience 1958), in the current edition of "McCutcheon's Emulsifiers & Detergents" published by the McCutcheon division of Manufacturing Confectioners Company or in "Tensid-Taschenbuch", H. Stache, 2nd Edn., Carl Hanser Verlag, München & Wien, 1981.

NON-IONIC SURFACTANTS

Nonionic detergent surfactants are well-known in the art. They normally consist of a water-solubilizing polyalkoxylene or a mono- or di-alkanolamide group in chemical combination with an organic hydrophobic group derived, for example, from alkylphenols in which the alkyl group contains from about 6 to about 12 carbon atoms, dialkylphenols in which each alkyl group contains from 6 to 12 carbon atoms, primary, secondary or tertiary aliphatic alcohols (or alkyl-capped derivatives thereof), preferably having from 8 to 20 carbon atoms, monocarboxylic acids having from 10 to about 24 carbon atoms in the alkyl group and polyoxypropylenes.

Also common are fatty acid mono- and dialkanolamides in which the alkyl group of the fatty acid radical contains from 10 to about 20 carbon atoms and the alkyloyl group having from 1 to 3 carbon atoms. In any of the mono- and di- alkanolamide derivatives, optionally, there may be a polyoxyalkylene moiety joining the latter groups and the hydrophobic part of the molecule.

In all polyalkoxylene containing surfactants, the polyalkoxylene moiety usually consists of an average of from 2 to 20 groups of ethylene oxide or of ethylene oxide and propylene oxide groups. The latter class includes those described in the applicants' published European specification EP-A-225,654, especially for use as all or part of the liquid phase.

Yet again, in some embodiments, preferred additional liquid nonionic surfactants include those formed from fatty alcohols condensed with both ethylene oxide and propylene oxide. Typical examples of these include the condensation products of alcohols having an average of from 12 to 16 carbon atoms, with an average of from 2 to 8 ethylene oxide and from 1 to 5 propylene oxide groups per molecule.

Another class of suitable nonionics comprise the alkyl polysaccharides (polyglycosides/oligosaccharides) such as described in any of specifications U.S. Pat. Nos. 3,640,998, 3,346,558, 4,223,129; EP-A-92,355; EP-A-99,183; EP 70,074, '75, '76, '77; EP 75,994, '95, '96.

Mixtures of nonionic detergent surfactants with other detergent surfactants such as anionic, cationic or ampholytic detergent surfactants and soaps may also be used.

Preferably the level of nonionic surfactants in the composition is from 1 to 90% by weight, more preferably 5 to 75%, most preferably 20 to 60%.

ANIONIC SURFACTANTS

Examples of suitable anionic detergent surfactants are alkali metal, ammonium or alkylolamine salts of alkylbenzene sulphonates or primary alkyl sulphates having from 10 to 18 carbon atoms in the alkyl group, secondary alkly sulphonates and their corresponding sulphonic acids (e.g. compounds of formula $R^4$—$C(SO_3M)$—$R^5$ where $R^4$ and $R^5$ are straight or branched alkyl or alkenyl groups and M represents hydrogen or an alkali metal such as sodium, these compounds being prepared, for example, by sulphoxidation of paraffins or olefins), alkyl and alkylether sulphates having from 10 to 24 carbon atoms in the alkyl group, the alkylether sulphates having from 1 to 5 ethylene oxide groups, and olefin sulphonates prepared by sulphonation of C10–24 alpha-olefins and subsequent neutralization and hydrolysis of the sulphonation reaction product and all stable free acid forms of such anionic surfactants.

Compositions of the invention comprise a solid phase dispersed in the liquid phase. As used herein, the term "solids" is to be construed as referring to materials in the solid phase which are added to the composition and are dispersed therein in solid form, those solids which dissolve in the liquid phase and those in the liquid phase which solidify (undergo a phase change) in the composition, wherein they are then dispersed.

NON-AQUEOUS ORGANIC SOLVENT

In compositions of the present invention, it is also possible to incorporate a non-surfactant non-aqueous organic "solvent" into the liquid phase.

As a general rule, the most suitable liquids to choose for this purpose are those organic materials having polar molecules. In particular, those comprising a relatively lipophilic part and a relatively hydrophilic part, especially a hydrophilic part rich in electron lone pairs, tend to be well suited. This is completely in accordance with the observation that liquid surfactants, especially polyalkoxylated nonionics, are one preferred class of material for the liquid phase.

Non-surfactants which are suitable for use as the liquid phase include those having the preferred molecular forms referred to above although other kinds may be used, especially if combined with those of the former, more preferred types. In general, the non-surfactant solvents can be used alone or with in combination with liquid surfactants. Non-surfactant solvents which have molecular structures which fall into the former, more preferred category include ethers, polyethers, alkylamines and fatty amines, (especially di- and tri-alkyl- and/or fatty- N-substituted amines), alkyl (or fatty) amides and mono- and di- N-alkyl substituted derivatives thereof, alkyl (or fatty) carboxylic acid lower alkyl esters, ketones, aldehydes, and glycerides. Specific examples include respectively, di-alkyl ethers, polyethylene glycols, alkyl ketones (such as acetone) and glyceryl trialkylcarboxylates (such as glyceryl tri-acetate, hereinafter referred to as GTA), glycerol, propylene glycol, and sorbitol.

Many light solvents with little or no hydrophilic character are in most systems, to a small extent, unsuitable on their own. Examples of these are lower alcohols, such as ethanol, or higher alcohols, such as dodecanol, as well as alkanes and olefins. However, they can be combined with other liquid materials.

PROPORTION OF LIQUID PHASE

Preferably, the compositions of the invention contain the liquid phase (whether or not comprising liquid surfactant) in an amount of at least 10% by weight of the total composition. The amount of the liquid phase present in the composition may be as high as about 90%, but in most cases the practical amount will lie between 20 and 70% and preferably between 35 and 60% by weight of the composition.

SOLIDS CONTENT

If present, in general, the solids content of the product may be within a very wide range, for example from 10–90%, usually from 30–80% and preferably from 40–65% by weight of the final composition. The solid phase should be in particulate form and have a weight average particle size of less than 300 microns, preferably less than 200 microns, more preferably less than 100 microns, especially less than 20 microns. The particle size may even be of sub-micron size. The proper particle size can be obtained by using materials of the appropriate size or by milling the total product in a suitable milling apparatus. In order to control aggregation of the solid phase leading to unredispersible settling or setting of the composition, it is preferred to include a deflocculant therein.

OTHER INGREDIENTS

In addition to the components already discussed, there are very many other ingredients which can be incorporated in liquid cleaning products.

There is a very great range of such other ingredients and these will be choosen according to the intended use of the product. However, the greatest diversity is found in products for fabrics washing and/or conditioning. Many ingredients intended for that purpose will also find application in products for other applications (e.g. in hard surface cleaners and warewashing liquids).

HYDROPHOBICALLY MODIFIED MATERIALS

The physical stability of non-aqueous liquid detergent compositions according to the present invention can be even further improved and/or setting problems can be minimised, if hydrophobically modified dispersants (hereinafter termed HM materials) are used.

For the purpose of the present invention, a dispersant material is a material, of which the main purpose is to stabilise the composition. Hydrophobically modified dispersant materials are particulate materials, of which the outer surface has chemically been treated to reduce the hydrophilic nature thereof.

Preferred HM materials have a weight average particle size of from 0.005 to 5 micrometers, more preferred 0.01 to 3 micrometers, most preferred from 0.02 to 0.5 micrometer. The amount of the HM material is preferably from 0.1 to 10 by weight of the composition, more preferred 0.3 to 5%, most preferred from 1.0 to 4%.

Preferably the number of hydroxy- and/or acid-groups at the surface of the particles is reduced by the hydrophobic modification treatment. Suitable reactions include esterification or etherification of the hydrophilic groups. Preferably the hydrophobic modification treatment involves at least 10% of the hydrophilic groups at the surface of the particle, more preferably from 40 to 95%, most preferably from 50 to 90%. Partial hydrophobing is preferred over complete hydrophobic modification.

Preferably HM silica containing dispersants are used. The hydrophobic modification of the silica particles preferably involves the substitution of the free hydroxy-groups at the outer surface of the silica particles by a short alkyl or silyl group. More preferably the surface hydroxy-groups are substituted by methyl groups.

For even greater reduction the clear layer separation of liquid detergent compositions of the invention, it has been found that the use of particulate metal oxides is especially advantageous. Preferred suspended metal oxides have a bulk density of 200 to 1,000 g/l, more preferred 250 to 800 g/l, especially preferably 300 to 700 g/l, most preferably from 400 to 650 g/l.

Preferably, the metal oxide is selected from calcium oxide, magnesium oxide, silicon dioxide and aluminium oxide, most preferably magnesium oxide is used.

The weight average particle size of the metal oxide is preferably from 0.1 to 200 micrometers, more preferably from 0.5 to 100 micrometers, most preferably from 2 to 70 micrometers. The level of metal oxide is preferably from 0.1 to 7% by weight of the composition, more preferably from 0.5 to 5%, most preferably from 1 to 4%.

Appropriate clays may also be incorporated to fulfil this purpose, and/or for fabric softening.

DETERGENCY BUILDERS

The detergency builders are those materials which counteract the effects of calcium, or other ion, water hardness, either by precipitation or by an ion sequestering effect. They comprise both inorganic and organic builders. They may also be sub-divided into the phosphorus-containing and non-phosphorus types, the latter being preferred when environmental considerations are important.

In general, the inorganic builders comprise the various phosphate-, carbonate-, silicate-, borate- and aluminosilicates-type materials, particularly the alkali-metal salt forms. Mixtures of these may also be used.

Examples of phosphorus-containing inorganic builders, when present, include the water-soluble salts, especially alkali metal pyrophosphates, orthophosphates, polyphosphates and phosphonates. Specific examples of inorganic phosphate builders include sodium and potassium tripolyphosphates, phosphates and hexametaphosphates.

Examples of non-phosphorus-containing inorganic builders, when present, include water-soluble alkali metal carbonates, bicarbonates, borates, silicates, metasilicates, and crystalline and amorphous aluminosilicates. Specific examples include sodium carbonate (with or without calcite seeds), potassium carbonate, sodium and potassium bicarbonates, silicates and zeolites.

Examples of organic builders include the alkali metal, ammonium and substituted ammonium, citrates, succinates, malonates, fatty acid sulphonates, carboxymethoxy succinates, ammonium polyacetates, carboxylates, polycarboxylates, aminopolycarboxylates, polyacetyl carboxylates and polyhydroxsulphonates. Specific examples include sodium, potassium, lithium, ammonium and substituted ammonium salts of ethylenediaminetetraacetic acid, nitrilotriacetic acid, oxydisuccinic acid, melitic acid, benzene polycarboxylic acids and citric acid. Other examples are organic phosphonate type sequestering agents such as those sold by Monsanto under the tradename of the Dequest range and alkanehydroxy phosphonates.

Other suitable organic builders include the higher molecular weight polymers and co-polymers known to have builder properties, for example appropriate polyacrylic acid, polymaleic acid and polyacrylic/ polymaleic acid co-polymers and their salts, such as those sold by BASF under the Sokalan Trade Mark. Referably the level of builder materials is from 0–60%, more preferred 5–50, most preferred 10–40% by weight.

DEFLOCCULANT

Preferably compositions of the invention also comprise one or more deflocculant materials. In principle, any material may be used as a deflocculant provided it fulfils the defloccuation test described in European Patent Specification EP-A-266 199 (Unilever). The capability of a substance to act as a deflocculant will partly depend on the solids/liquid phase combination. However, especially preferred are acids.

Some typical examples of deflocculants include the alkanoic acids such as acetic, propionic and stearic acids and their halogenated counterparts such as trichloracetic and trifluoracetic as well as the alkyl (e.g. methane) sulphonic acids and aralkyl (e.g. paratoluene) sulphonic acids.

Examples of suitable inorganic mineral acids and their salts are hydrochloric, carbonic, sulphurous, sulphuric and phosphoric acids; potassium monohydrogen sulphate, sodium monohydrogen sulphate, potassium monohydrogen phosphate, potassium dihydrogen phosphate, sodium monohydrogen phosphate, potassium dihydrogen pyrophosphate, tetrasodium monohydrogen triphosphate.

Other organic acids may also be used as deflocculants, for example formic, lactic, amino acetic, benzoic, salicylic, phthalic, nicotinic, ascorbic, ethylenediamine tetraacetic, and aminophosphonic acids, as well as longer chain fatty carboxylates and triglycerides, such as oleic, stearic, lauric acid and the like. Peracids such as percarboxylic and persulphonic acids may also be used, functioning as both a deflocculant and a bleach.

The class of acid deflocculants further extends to the Lewis acids, including the anhydrides of inorganic and organic acids. Examples of these are acetic anhydride, maleic anhydride, phthalic anhydride and succinic anhydride, sulphur-trioxide, diphosphorous pentoxide, boron trifluoride, antimony pentachloride.

"Fatty" anions are very suitable deflocculants, and a particularly preferred class of deflocculants comprises anionic surfactants. Although anionics which are salts of alkali or other metals may be used, particularly preferred are the free acid forms of these surfactants (wherein the metal cation is replaced by an H+ cation, i.e. proton). These anionic surfactants include all those classes, sub-classes and specific forms described in the aforementioned general references on surfactants, viz, Schwartz & Perry, Schwartz Perry and Berch, McCutcheon's, Tensid-Taschenbuch; and the free acid forms of such surfactants. Many anionic surfactants have already been described hereinbefore. In the role of deflocculants, the free acid forms of these are generally preferred.

In particular, some preferred sub-classes and examples are the C10–C22 fatty acids and dimers thereof, the C8–C18 alkylbenzene sulphonic acids, the C10–C18 alkyl- or alkylether sulphuric acid monoesters, the C12–C18 paraffin sulphonic acids, the fatty acid sulphonic acids, the benzene-, toluene-, xylene- and cumene sulphonic acids and so on. Particularly preferred are the linear C12–C18 alkylbenzene sulphonic acids.

As well as anionic surfactants, zwitterionic-types can also be used as deflocculants. These may be any described in the aforementioned general surfactant references. One example is lecithin.

The level of the deflocculant material in the composition can be optimised by the means described in the aforementioned EP-A-266 199, but in very many cases is at least 0.01%, usually 0.1% and preferably at least 1% by weight, and may be as high as 15% by weight. For most practical purposes, the amount ranges from 2–12%, preferably from 4–10% by weight, based on the final composition. Surprisingly, however it has been found that for obtaining stability, in compositions of the invention generally the presence of the polymer material reduces the need for high levels of deflocculant material.

BLEACH SYSTEM

The compositions of the present invention preferably include a bleach. Suitable bleaches include the halogen, particularly chlorine bleaches such as are provided in the form of alkalimetal hypohalites, e.g. hypochlorites. In the application of fabrics washing, the oxygen bleaches are preferred, for example in the form of an inorganic persalt, preferably with a bleach precursor, or as a peroxy acid compound. In a more preferred embodiment, the composition will also comprise a bleach catalyst.

In the case of the inorganic persalt bleaches, the activator makes the bleaching more effective at lower temperatures, i.e. in the range from ambient temperature to about 60° C., so that such bleach systems are commonly known as low-temperature bleach systems and are well-known in the art. The inorganic persalt such as sodium perborate, both the monohydrate and the tetrahydrate, acts to release active oxygen in solution, and the activator is usually an organic compound having one or more reactive acyl residues, which cause the formation of peracids, the latter providing for a more effective bleaching action at lower temperatures than the peroxybleach compound alone.

A typical precursor is tetraacetyl ethylene diamine (hereinafter called TAED). The ratio by weight of the peroxybleach compound to the activator is from about 20:1 to about 2:1, preferably from about 10:1 to about 3.5:1. Whilst the amount of the bleach system, i.e. peroxybleach compound and activator, may be varied between about 5% and about 50% by weight of the total liquid, it is preferred to use from about 6% to about 30% of the ingredients forming the bleach system. Thus, the preferred level of the peroxybleach compound in the composition is between about 5.5% and about 27% by weight, while the preferred level of the activator is between about 0.5% and about 14%, most preferably between about 1% and about 7% by weight.

Typical examples of the suitable peroxybleach compounds are alkalimetal perborates, both tetrahydrates and monohydrates, alkali metal percarbonates, persilicates and perphosphates, of which sodium perborate is preferred.

A particularly suitable bleach catalyst usable herein in combination with an oxygen bleach in the form of an inorganic persalt with or without a bleach precursor or as a peroxyacid compound, is a dinuclear manganese (III)—or Manganese (IV) complex as described in Applicant's co-pending European Patent Application Nos. 91201171.5 and 91201172.3.

Preferred catalysts of this class are those referred to as having the following formulae:
1) $[Mn^{IV}_2(m\text{-}O)_3(Me\text{-}TACN)_2](PF_6)_2$
2) $[Mn^{IV}_2(m\text{-}O)_3(Me/Me\text{-}TACN)_2](PF_6)_2$
3) $[Mn^{III}_2(m\text{-}O)(m\text{-}OAc)_2(Me\text{-}TACN)_2](PF_6)_2$
4) $[Mn^{III}_2(m\text{-}O)(m\text{-}OAc)_2(Me/Me\text{-}TACN)_2](PF_6)_2$ Wherein Me-TACN is 1,4,7-trimethyl-1,4,7-triazacyclononane, and Me/Me-TACN is 1,2,4,7-tetramethyl-1,4,7-triazacyclononane.

These catalysts may be used in the present invention in an amount corresponding to a Manganese level of from about 0.0001 to about 1.0% by weight, preferably from about 0.0005 to about 0.5% by weight.

It is particularly preferred to include in the compositions, a stabiliser for the bleach or bleach system, for example ethylene diamine tetramethylene phosphonate and diethylene triamine pentamethylene phosphonate or other appropriate organic phosphonate or salt thereof, such as the Dequest range hereinbefore described. These stabilisers can be used in acid or salt form, such as the calcium, magnesium, zinc or aluminium salt form. The stabiliser may be present at a level of up to about 1% by weight, preferably between about 0.1% and about 0.5% by weight.

The applicants have also found that liquid bleach precursors, such as glycerol triacetate and ethylidene heptanoate acetate, isopropenyl acetate and the like, also function suitably as a material for the liquid phase, thus obviating or reducing any need of additional relatively volatile solvents, such as the lower alkanols, paraffins, glycols and glycolethers and the like, e.g. for viscosity control.

MISCELLANEOUS OTHER INGREDIENTS

Other ingredients comprise those remaining ingredients which may be used in liquid cleaning products, such as fabric conditioning agents, enzymes, perfumes (including deoperfumes), micro-biocides, colouring agents, fluorescers, soil-suspending agents (anti-redeposition agents), corrosion inhibitors, enzyme stabilising agents, and lather depressants.

Amongst the fabric conditioning agents which may be used, either in fabric washing liquids or in rinse conditioners, are fabric softening materials such as fabric softening clays, quaternary ammonium salts, imidazolinium salts, fatty amines and cellulases. Enzymes which can be used in liquids according to the present invention include proteolytic enzymes, amylolytic enzymes and lipolytic enzymes (lipases). Various types of proteolytic enzymes and amylolytic enzymes are known in the art and are commercially available. They may be incorporated as "prills", "marumes" or suspensions.

The fluorescent agents which can be used in the liquid cleaning products according to the invention are well known and many such fluorescent agents are available commercially. Usually, these fluorescent agents are supplied and used in the form of their alkali metal salts, for example, the sodium salts. The total amount of the fluorescent agent or agents used in a detergent composition is generally from 0.02-2% by weight.

When it is desired to include anti-redeposition agents in the liquid cleaning products, the amount thereof is normally from about 0.1% to about 5% by weight, preferably from about 0.2% to about 2.5% by weight of the total liquid composition. Preferred anti-redeposition agents include carboxy derivatives of sugars and celluloses, e.g. sodium carboxymethyl cellulose (hereinafter referred to as SCMC), anionic poly-electrolytes, especially polymeric aliphatic carboxylates, or organic phosphonates.

WATER

The compositions are substantially non-aqueous, i.e. they contain little or no free water in the liquid phase, preferably no more than 5%, preferably less than 3%, especially equal to or less than 1.5% by weight of the total composition. It has been found that the higher the water content, the more likely it is for the viscosity to be too high, or even for setting to occur.

USE

Composition in accordance with the present invention may be used for several detergency purposes, for example the cleaning of surfaces and the washing of fabrics. For the washing of fabrics, preferably an aqueous liquor containing 0.1 to 10%, more preferably 0.2 to 2%, of the non-aqueous detergent composition of the invention is used.

PROCESSING

During manufacture, it is preferred that all raw materials should be dry and (in the case of hydratable salts) in a low hydration state, e.g. anhydrous phosphate builder, sodium perborate monohydrate and dry calcite abrasive, where these are employed in the composition. In a preferred process, the dry, substantially anhydrous solids are blended with the liquid phase in a dry vessel. If deflocculant materials are used, these should preferably—at least partly—be mixed with the liquid phase, prior to the addition of the solids. In order to minimise the rate of sedimentation of the solids, this blend is passed through a grinding mill or a combination of mills, e.g. a colloid mill, a corundum disc mill, a horizontal or vertical agitated ball mill, to achieve a particle size of 0.1 to 100 microns, preferably 0.5 to 50 microns, ideally 1 to 10 microns. A preferred combination of such mills is a colloid mill followed by a horizontal ball mill since these can be operated under the conditions required to provide a narrow size distribution in the final product. Of course particulate material already having the desired particle size need not be subjected to this procedure and if desired, can be incorporated during a later stage of processing.

During this milling procedure, the energy input results in a temperature rise in the product and the liberation of air entrapped in or between the particles of the solid ingredients. It is therefore highly desirable to mix any heat sensitive ingredients into the product after the milling stage and a subsequent cooling step. It may also be desirable to de-aerate the product before addition of these (usually minor) ingredients and optionally, at any other stage of the process. Typical ingredients which might be added at this stage are perfumes and enzymes, but might also include highly temperature sensitive bleach components or volatile solvent components which may be desirable in the final composition. However, it is especially preferred that volatile material be introduced after any step of deaeration. Suitable equipment for cooling (e.g. heat exchangers) and de-aeration will be known to those skilled in the art.

It follows that all equipment used in this process should preferably be completely dry, special care being taken after any cleaning operations. The same is true for subsequent storage and packing equipment.

EXAMPLES

| Component | % by weight |
|---|---|
| Vista Novel 1012-62 (1) | 22.9 |
| Additional Nonionic | 19.0 |
| Glycerol triacetate | 5.0 |
| DB100 (2) | 1.2 |
| Marlon AS-3 (3) | 6.0 |
| Sodium Carbonate | 16.7 |
| Calcite | 6.0 |
| Versa TL-3 (4) | 1.5 |
| Sipernat D17 (5) | 3.0 |
| TAED | 5.0 |
| Sodium Perborate | 10.5 |
| SCMC | 1.5 |
| Tinopal CBS-X | 0.15 |
| Enzyme + Perfume | 1.55 |

(1) Nonionic surfactant, a $C_{10}$–$C_{21}$ fatty alchol ethoxylated with an average of six ethylene oxide groups per mole, ex Vista
(2) Silicone oil antifoam agent ex Dow Corning
(3) Dodecyl benzene sulphonic acid, ex Huls
(4) A polymer, ex National Starch & Chemical Co.
(5) A silica, ex Degussa

| Example | Additional Nonionic |
|---|---|
| A | Synperonic A3 (6) |
| 1 | Etocas (7) |

(6) A $C_{11}$–$C_{13}$ fatty alcohol ethoxylated with an average of three ethylene oxide groups per molecule, ex ICI
(7) A compound of formula (I) as hereinbefore defined, wherein $R^1$–$R^3$ are the same and n is 10, ex Croda.

Thus Example A is excomposition of known kind and composition 1 is a composition according to the present invention.

After 2 weeks storage at room temperature, the composition of Example A showed a 3 mm clear layer formation due to sedimentation of the solids whilst the composition of Example 1 showed an improved clear layer formation of only 1 mm.

The following parameters were also measured for both formulation.

|  | Ex A | Ex 1 |
|---|---|---|
| Freezing Point | 5° C. | 0° C. |
| Residual bleach index after 4 weeks at 37° C. | 9.9 | 10.0 |
| Bleach precursor stability index | 4.0 | 5.6 |

It can be seen that the composition of Example 1 showed considerably better low temperature tolerance, approximately the same bleach stability and significantly better bleach precursor stability in comparison with the composition of Example A.

We claim:

1. A heterogeneous, two-phase, substantially non-aqueous liquid cleaning composition having no more than 5% by wt. water, comprising a non-aqueous liquid phase and a particulate solid phase dispersed in the non-aqueous liquid phase selected from the group consisting of bleaches, bleach activators, builders and solid surfactants which liquid phase comprises from 10–90% by wt. of the liquid phase of a polyalkoxylated castor oil derivative.

2. A composition according to claim 1, wherein the polyalkoxylated castor oil derivative has the general formula (I):

where $R^1$–$R^3$ are independently selected from groups of formula:

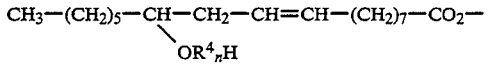

where n is from 2 to 16 and each $R^4$ is independently selected from $C_{2-4}$ alkyleneoxy groups.

3. A composition according to claim 2, wherein $R^1$ to $R^3$ are the same.

4. A substantially non-aqueous liquid cleaning product composition comprising a non-aqueous liquid phase and a particulate solid phase dispersed in the non-aqueous liquid phase, which liquid phase comprises from 10–90% by wt. of the liquid phase of a compound of formula (III)

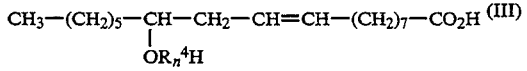

or a salt thereof, wherein $R^4$ is independently selected from $C_{2-4}$ alkyleneoxy groups and n is from 2 to 16 or a compound of formula (IV)

$$R^6-(CH_2)_2-R^7$$

wherein $R^6$ is a group of formula

or a group of formula

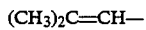

and $R^7$ is a group of formula

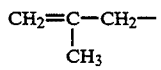

a group of formula

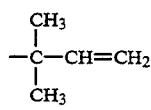

or a group of formula

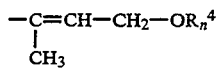

wherein $R^4$ is independently selected from $C_{2-4}$ alkyleneoxy groups and n is from 2 to 16.

5. A composition according to claim 1, wherein the liquid phase further comprises from 10–90% by wt. of the liquid phase of a polyalkoxylated fatty alcohol adduct wherein the polyalkoxylated fatty alcohol adduct is a liquid condensation product of a $C_8$–$C_{20}$ fatty alcohol with from 2 to 20 moles of ethylene oxide.

* * * * *